United States Patent [19]
Gioco et al.

[11] Patent Number: 5,565,466
[45] Date of Patent: Oct. 15, 1996

[54] METHODS FOR MODULATING THE HUMAN SEXUAL RESPONSE

[75] Inventors: Diane-Marie Gioco, West Haven, Conn.; Adrian Zorgniotti, deceased, late of Wyland, Mass., by Flavia Zorgniotti, executrix

[73] Assignee: Zonagen, Inc., The Woodlands, Tex.

[21] Appl. No.: 286,615

[22] Filed: Aug. 9, 1994

Related U.S. Application Data

[63] Continuation of Ser. No. 106,434, Aug. 13, 1993, abandoned.

[51] Int. Cl.$^6$ ................................................. A61K 31/44
[52] U.S. Cl. .................. 514/280; 514/644; 514/471; 514/649; 514/400; 514/396; 514/307; 514/509; 514/532; 514/523; 514/212
[58] Field of Search ................................. 514/248, 280, 514/684, 471, 649, 400, 396, 307, 509, 532, 523, 212

[56] References Cited

U.S. PATENT DOCUMENTS

| | | |
|---|---|---|
| 3,943,246 | 3/1976 | Sturmer . |
| 4,127,118 | 11/1978 | Latorre . |
| 4,139,617 | 2/1979 | Grunwell et al. . |
| 4,530,920 | 7/1985 | Nestor et al. . |
| 4,801,587 | 1/1989 | Voss et al. . |
| 4,863,911 | 9/1989 | Anderson, Jr. et al. . |
| 4,885,173 | 12/1989 | Stanley et al. . |
| 5,059,603 | 10/1991 | Rubin . |
| 5,065,744 | 11/1991 | Zusmanovsky . |
| 5,145,852 | 9/1992 | Virag . |
| 5,236,904 | 8/1993 | Gerstenberg et al. . |
| 5,256,652 | 10/1993 | El-Rashidy . |
| 5,270,323 | 12/1993 | Milne, Jr. et al. . |
| 5,399,581 | 3/1995 | Laragh et al. ............... 514/248 |

OTHER PUBLICATIONS

Althof, S. E. et al., Sexual, psychological, and marital impact of self-injection of papaverine and phentolamine; a long-term prospective study, *J. Sex & Marital Ther.*, 17(2):101–112 (1991).

Azadzoi, K. M. et al., Effects of Intracavernosal Trazadone Hydrochloride; Animal and Human Studies, *J. Urol.*, 144(5):1277–1282 (1990).

Brindley, G. S., Cavernosal Alpha–Blockade: A New Technique for Investigating and treating Erectile Impotence, *Brit. J. Psychiat.*, 143:332–337 (1983).

Brindley, G. S., Cavernosal alpha–blockade and human penile erection, *J. Physiol.*, 342:24P (1983).

Brindley, G. S., Pilot experiments on the actions of drugs injected into the human *corpus cavernosum* penis, *Br. J. Pharmac.* 87: 495–500 (1986).

Corriere, Jr. et al., Development of Fibrotic Penile Lesions Secondary to the Intracorporeal Injection of Vasoactive Agents, *J. Urol.*, 140:615–617 (1988).

Gwinup, G., Oral Phentolamine in Nonspecific Erectile Insufficiency, *Ann. Int. Med.*, 15 Jul. 1988, 162–163.

Larsen, E. H. et al., Fibrosis of Corpus Cavernosum after Intracavernous Injection of Phentolamine/Papaverine, *J. Urol.*, 137:292–293 (1987).

Sonda, L. P. et al., The Role of Yohimbine for the Treatment of Erectile Impotence, *J. Sex & Marital Ther.*, 16(1):15–21 (1990).

Virag, R., Intracavernous Injection of Papaverine for Erectile Failure, *Lancet*, ii:938 (1984).

Virag, R. et al., Intracavernous Injection of Papaverine as a Diagnostic and Therapeutic Method in Erectile Failure, *Angiology*, 35:79–87 (1984).

Zorgniotti, A. W. et al., Auto–Injection of the Corpus Cavernosum with a Vasoactive Drug Combination for Vasculogenic Impotence, *J. Urol.*, 133:39–41 (1985).

*Primary Examiner*—Marianne M. Cintins
*Assistant Examiner*—Keith MacMillan
*Attorney, Agent, or Firm*—Marshall, O'Toole, Gerstein, Murray & Borun

[57] ABSTRACT

The invention is directed to improved methods for modulating the human sexual response by administering a vasodilator to the circulation by a route of administration that avoids the "first-pass" effect.

17 Claims, 1 Drawing Sheet

FIGURE 1

METHODS FOR MODULATING THE HUMAN SEXUAL RESPONSE

CROSS REFERENCE TO RELATED APPLICATIONS

This application is a continuation-in-part of commonly-assigned U.S. patent application Ser. No. 08/106,434, filed Aug. 13, 1993 now abandoned.

FIELD OF THE INVENTION

The application is directed to improved methods for modulating the human sexual response by administering vasodilator agents to the circulation of a human via transmucosal, transdermal, intranasal or rectal routes of administration that obviate "first-pass" deleterious effects on such agents.

BACKGROUND OF THE INVENTION

The human sexual response in both males and females results from a complex interplay of psychological, hormonal, and other physiological influences. One important aspect of human sexual response that is common to both men and women is the erectile response which itself results from an interplay between the autonomic nervous system, the endocrine system, and the circulatory system.

Failure of the erectile response is most common in men and is referred to as impotence. Impotence is the inability of a male to achieve or sustain a penile erection sufficient for vaginal penetration and intercourse. Numerous approaches have been taken in attempts to treat impotence. These approaches include the use of external or internally implanted penile prosthesis. (See, e.g., U.S. Pat. No. 5,065, 744,to Zumanowsky). A variety of drugs and methods for administering drugs have also been used in attempts to treat impotence. For example, U.S. Pat. No. 3,943,246 to St ürmer addresses treatment of impotence in men by buccal and peroral administration of daily doses of 300–1500 international units (I.U.) of oxytocin or daily divided doses of 150–250 I.U. of desamino-oxytocin. The patent states that the buccal administration of 100 I.U. three times a day for 14 days results in improvement of impotentia erectionis in 12 of the 16 patients treated.

U.S. Pat. No. 4,530,920 to Nestor et al. suggests the possibility that administration of nonapeptide and decapeptide analogs of luteinizing hormone releasing hormone agonists may be useful in the induction or enhancement of sexual behavior or therapy for impotence or frigidity. Nestor et al. suggest numerous routes of administration of the analogs including buccal, sublingual, oral, parenteral (including subcutaneous, intramuscular, and intravenous administration), rectal, vaginal, and others.

U.S. Pat. No. 4,139,617 to Grunwell et al. suggests buccal and other routes of administration of 19-oxygenated-androst-5-enes for the endocrine mediated enhancement of the libido in humans.

U.S. Pat. No. 4,863,911 to Anderson et al. addresses methods for treating sexual dysfunction in mammals using a biooxidizable, blood-brain barrier penetrating estrogen derivative. One of the purported objects of the Anderson et al. invention is the treatment of "psychological impotence" in males. Test results showed that the drugs used in the study stimulated mounting behavior, intromission, and mount latency in castrated rats.

A number of publications have proposed the use of various vasodilators for the treatment of impotence in males. Attempts to utilize vasodilators for the treatment of impotence were prompted because a significant percentage of cases of impotence were noted to be vasculogenic, i.e., resulting from vascular insufficiency.

Voss et at., U.S. Pat. No. 4,801,587, issued Jan. 31, 1989, addresses the use of an ointment containing a vasodilator and a carrier agent for topical application to the penis of impotent men. The Voss et al. patent also describes application of such an ointment into the urethra of the penis using a catheter as well as a multi-step regimen for applying a vasodilator to the skin of the penis. In addition, Voss et at. proposes the surgical removal of a portion of the fibrous sheath surrounding the corpora cavernosum, thereby facilitating the penetration of a vasodilator-containing ointment into the corpora cavernosum. Vasodilators suggested for use by Voss et at. include papaverine, hydralazine, sodium nitroprusside, phenoxybenzamine, and phentolamine. The Voss et at. patent, however, provides no information regarding the actual efficacy of the treatments proposed or the nature of the response to such treatments.

U.S. Pat. No. 4,127,118 to Latorre describes treating male impotence by directly injecting the vasodilating drugs into the corpus cavernosum and the corpus spongiosum of the penis using a syringe and one or more hypodermic needles. More particularly, the Latorre patent proposes the intracavernosal and intraspongiosal injection of sympathomimetic amines such as nylidrin hydrochloride, adrenergic blocking agents such as tolazoline o hydrochloride, and direct acting vasodilators such as isoxsuprine hydrochloride and nicotinyl alcohol.

Brindley, G.S. (*Br. J. Pharmac.* 87:495–500 1986) showed that, when injected directly into the corpus cavernosum using a hypodermic needle, certain smooth muscle relaxing drugs including phenoxybenzamine, phentolamine, thymoxamine, imipramine, verapamil, papaverine, and naftidrofuryl caused erection. This study noted that injection of an "appropriate dose of phenoxybenzamine or papaverine is followed by an unrelenting erection lasting for hours." Injection of the other drugs studied induced erections lasting from about 11 minutes to about 6.5 hours. Zorgniotti et al., *J. Urol.* 133:39–41 (1985) demonstrated that the intracacernosal injection of a combination of papaverine and phentolamine could result in an erection in otherwise impotent men. Similarly, Althof et al. *J. Sex Marital Ther* 17(2): 101–112 (1991) reported that intracavernosal injection of papaverine hydrochloride and phentolamine mesylate resulted in improved erectile ability in about 84% of patients injected. However, in that study the dropout rate was 57%, fibrotic nodules developed in 26% of the patients, 30% of the patients developed abnormal liver function values, and bruising occurred in 19% of the patients.

Other studies describing intracavernosal injection of drugs using hypodermic needles for the treatment of impotence include: Brindley, *J. Physiol* 342:24P (1983); Brindley, *Br. J. Psychiatr* 143:312–337 (1983); Virag, *Lancet* ii:978 (1982); and Virag, et al., *Angiology* 35:79–87 (1984).

While intracavernosal injection may be useful for inducing erections in impotent men, the technique has numerous drawbacks. Obvious drawbacks include pain, risk of infection, inconvenience and interference with the spontaneity of the sex act. Priapism (prolonged and other painful erection) also appears to be a potential problem when using injection methods. See, e.g. Brindley, (1986). Another problem arising in some cases of intracavernosal injection involves the formation of fibrotic lesions in the penis. See, e.g., Corriere, et al., *J. Urol.* 140:615–617 (1988) and Larsen, et at., *J. Urol.* 137:292–293 (1987).

Phentolamine, which has been shown to have the potential to induce erection when injected intracavernosally, has also been the subject of oral administration to test its effects in men having non-specific erectile insufficiency (Gwinup, *Ann. Int. Med.* 15 Jul. 1988, pp. 162–163). In that study, 16 patients ingested either a placebo or a 50 mg orally administered dose of phentolamine. Eleven of the 16 patients (including three placebo-treated patients) became tumescent, became more responsive to sexual stimulation, and were able to achieve an erection sufficient for vaginal penetration after waiting 1.5 hours to attempt intercourse.

Sonda et al. *J. Sex & Marital Ther.* 16(1): 15–21 (year) reported that yohimbine ingestion resulted in subjective improvement in erectile ability in 38% of impotent men treated, but only 5% of the treated patients reported complete satisfaction.

Of interest to the background of the invention are the disclosures of Stanley et al., U.S. Pat. No. 4,885,173, which addresses methods for non-invasively administering drugs having cardiovascular or renal vascular activity through use of a lollipop assertedly facilitating drug absorption through the mucosal tissues of the mouth, pharynx, and esophagus. The Stanley et al. patent proposes that a large number of lollipop-administered drugs may improve cardiovascular function including drugs exhibiting direct vasodilating effects, calcium channel blockers, β-adrenergic blocking agents, serotonin receptor blocking agents, angina blocking agents, other antihypertensive agents, cardiac stimulating agents, and agents which improve renal vascular function.

U.S. Pat. No. 5,059,603 to Rubin describes the topical administration to the penis of isoxsuprine and caffeine, and nitroglycerine and caffeine along with suitable carrier compounds for the treatment of impotence.

There continues to exist a need in the art for effective means for modulating human sexual response and especially for enhancing erectile ability in males suffering from impotence. Ideally, such means would be convenient and simple to use, would not require a constant dosage regimen or even multiple doses to achieve desired results, would be non-invasive and would allow a rapid and predictable capacity for onset of erectile function on demand and in response to normal sexual stimulation.

SUMMARY OF THE INVENTION

The present invention provides improved methods for modulating the human sexual response in a human by administering a vasodilator agent to the circulation in an amount effective to increase blood flow to the genitalia. According to the invention, modulation of male and female human sexual response is provided on demand by administering an effective vasodilating amount of the agent by a route selected from the group consisting of transmucosal, transdermal, intranasal and rectal. Vasodilating agents useful in the present invention include, but are not limited to, the group consisting of phentolamine mesylate, phentolamine hydrochloride, phenoxybenzamine, yohimbine, organic nitrates (e.g. nitroglycerin), thymoxamine, imipramine, verapamil, isoxsuprine, naftidrofuryl, tolazoline and papaverine. The presently preferred agent is phentolamine mesylate. The presently preferred administrative route is transmucosal, especially buccal.

The present invention is specifically directed to improved methods for treating male impotence by administering a vasodilator agent in an amount effective to increase blood flow to the penis wherein erectile ability on demand is permitted by administering the agent by an administrative route selected from the group consisting of transmucosal, transdermal, intranasal, and rectal.

Preferably, the amount of vasodilating agent used in the practice of the invention for treatment of male impotence is effective to improve erectile ability in from about 1 minute to about 60 minutes following administration of the agent.

The invention is also specifically directed to methods for modulating the excitation and plateau phases of the female sexual response on demand by transmucosal, transdermal, intranasal, or rectal administration of an effective amount of vasodilator agent.

The methods of the present invention are also useful in preparation for sexual intercourse by virtue of the ability to modulate the sexual response in both males and females.

The present invention is also directed to the use of a drug having vasodilator activity for the manufacture of a medicament for transmucosal, transdermal, intranasal, and rectal administration to modulate sexual response in a human. Vasodilator drugs useful for manufacturing the medicament include, but are not limited to, phentolamine mesylate, phentolamine hydrochloride, phenoxybenzamine yohimbine, organic nitrates, thymoxamine, imipramine, verapamil, isoxsuprine, naftidrofuryl, tolazoline, and papaverine.

Numerous other advantages of the present invention will be apparent from the following detailed description of the invention including the accompanying examples and the appended claims.

DETAILED DESCRIPTION

The human sexual response in both the male and female involves a complex interplay between endocrine, neurological and psychological components which result in certain physiological and anatomical responses in both men and women.

While there are obvious differences in the sexual response between men and women, one common aspect of the sexual response is the erectile response. The erectile response in both males and females is result of engorgement of the erectile tissues of the genitalia with blood in response to sexual stimulation (physical, psychological, or both).

The vasculature which serves erectile tissue in both men and women is similar. In particular, in both men and women, the arterial circulation to the erectile tissues of the genitalia derives from the common iliac artery which branches from abdominal aorta. The common iliac artery bifurcates into the internal and external iliac arteries. The internal pudic artery arises from the smaller of two terminal branches of the anterior trunk of the internal iliac artery. In the female, the internal pudic artery branches into the superficial perineal artery which supplies the labia pudenda. The internal pudic artery also branches into the artery of the bulb which supplies the bulbi vestibuli and the erectile tissue of the vagina. The artery of the corpus cavernosum, another branch of the internal pudic artery supplies the cavernous body of the clitoris. Still another branch of the internal pudic artery is the arteria dorsalis clitoridis which supplies the dorsum of the clitoris and terminates in the glans and membranous folds surrounding the clitoris which correspond to the prepuce of the male.

In the male, the internal pudic artery branches into the dorsal artery of the penis (which itself branches into a left and right branch) and the artery of the corpus cavernosum, all of which supply blood to the corpus cavernosum. The dorsal artery of the penis is analogous to the artery dorsalis clitoridis in the female, while the artery of the corpus cavernosum in the male is analogous to the artery of the same name in the female.

The male erectile response is regulated by the autonomic nervous system which controls blood flow to the penis via the interaction of peripheral nerves associated with the arterial vessels in and around the corpus cavernosum. In the non-aroused or non-erect state, the arteries serving the o corpus cavernosum are maintained in a relatively constricted state, thereby limiting the blood flow to the corpus cavernosum. However, in the aroused state, the smooth muscles associated with the arteries relax under the influence of catecholamines and blood flow to the corpus cavernosum greatly increases, causing expansion and rigidity of the penis. Brindley, supra (1986) hypothesizes that smooth muscle contraction opens valves through which blood can flow from the corpus cavernosum into the extracavernosal veins. According to Brindley (1986), when the relevant smooth muscles relax, the valves close diminishing venous outflow from the corpus cavernosum. When accompanied by increased arterial blood flow into the corpus cavernosum, this results in engorgement of the corpus cavernosum and an erection.

The pre-orgasmic sexual response in females can be broken down into distinct phases. Both the excitement phase and the plateau phase involve vasodilation and engorgement (vasocongestion) of the genitalia with arterial blood in a manner analogous to the male erectile response.

The excitement phase of the female sexual response is characterized by vasocongestion in the walls of the vagina which leads to the transudation of vaginal fluids and vaginal lubrication. Further, the inner one-third of the vaginal barrel expands and the cervix and the body of the uterus become elevated. This is accompanied by the flattening and elevation of the labia majora and an increase in clitoral size. [Kolodny et al., *Textbook of Sexual Medicine*, Little and Brown, Boston, Mass. (1979)].

The plateau phase follows the excitement phase in the female sexual response and is characterized by prominent vasocongestion in the outer one-third of the vagina, causing a narrowing of the opening of the vagina and a retraction of the shaft and the glans of the clitoris against the symphysis pubis. These responses are also accompanied by a marked vasocongestion of the labia. [Kolodny, supra (1979)].

The vasocongestive aspects of the female sexual response are not restricted to the genitalia in that areolar engorgement also occurs, sometimes to the extent that it masks the antecedent nipple erection that usually accompanies the excitement phase.

The failure of the erectile response in men to the extent that vaginal penetration and sexual intercourse cannot be achieved is termed impotence. Impotence has numerous possible causes which can be broken down into several general classifications. Endocrine related impotence can result from primary gonadal failure, advanced diabetes mellitus, hypothyroidism, and as one of the secondary sequelae of pituitary adenoma, idiopathic or acquired hypogonadism, hyperprolactinemia and other endocrine abnormalities.

Chronic systemic illnesses such as cirrhosis, chronic renal failure, malignancies and other systemic diseases can also cause impotence. Neurogenic impotence arising in the central nervous system can be caused by temporal lobe disorders caused by trauma, epilepsy, neoplasms and stroke, intramedullary spinal lesions, paraplegia, and demyelinating disorders. Neurogenic causes of impotence arising in the peripheral nervous system include somatic or autonomic neuropathies, pelvic neoplasms, granulomas, trauma, and others. Urologic causes of impotence include complete prostatectomy, local trauma, neoplasms, Peyronie's disease, and others.

As many as half the cases of male impotence may be psychogenic because there is no readily-ascertainable organic cause for the disorder. Even when there appears to be an underlying organic cause of impotence, psychologic factors may play a role in the disorder.

The present invention is designed to modify the circulatory aspects of the erectile response using vasoactive agents administered to the circulation by a route selected from the group consisting of transmucosal, transdermal, intranasal, and rectal.

A number of vasoactive agents may be used in the practice of the present invention based on demonstrated systemic efficacy as vasodilators. Useful vasodilating drugs include those generally classified as $\alpha$-adrenergic antagonists, sympathomimetic amines and those agents which exhibit direct relaxation of vascular smooth muscle. Exemplary $\alpha$-adrenergic antagonists include phentolamine hydrochloride, phentolamine mesylate, phenoxybenzamine, tolazoline, dibenamine, yohimbine, and others. Phentolamine mesylate is a preferred $\alpha$-adrenergic agent vasodilator for use preferred practice of the present invention. An exemplary sympathomimetic amine contemplated for use in the method of the present invention is nylidrin and use of other sympathomimetic amines having vasodilating activity is also contemplated.

Nicotinic acid (or nicotinyl alcohol) has a direct vasodilating activity useful in the practice of the present invention. Also contemplated is the use of papaverine, a non-specific smooth muscle relaxant which possesses vasodilating activity and which has been used to treat male impotence by direct injection into the corpus cavernosum either alone or in combination with other drugs such as phentolamine. Organic nitrates such as nitroglycerine and amyl nitrate have pronounced vasodilating activity by virtue of their ability to relax vascular smooth muscle and are thus contemplated for use according to the invention. Other vasoactive drugs useful in the practice of the present invention include, without limitation, thymoxamine, imipramine, verapamil, naftidrofuryl, and isoxsuprine.

In the practice of the present invention, vasoactive agents are administered by the transmucosal, intranasal, transdermal, or rectal routes of administration such that the agent is conveyed in circulation to the site of effect described below.

Oral administration of a drug in an attempt to effect delivery to a specific site within circulation may have several drawbacks. First, drug absorption is limited by gastrointestinal transit time and thus, the rapidity of onset of drug action may be limited. Second, the drug may be inactivated by (e.g. by hydrolysis) in the low pH environment of the stomach and or by other chemical or biochemical interactions in the intestines. Third, when an orally ingested drug reaches the intestine, it is absorbed into the portal circulation and delivered to the liver where it can be metabolized and inactivated. Hepatic inactivation following absorption of a drug from the gastrointestinal tract is referred to as "first-pass" effect or "presystemic" elimination and, along with poor absorption and slow transit times through the gastrointestinal tract, functions to require larger oral doses of drugs than may be necessary with other routes of administration. This, in turn, can account for delays in the onset of the therapeutic effect of a drug. [Goodman et al., *The Pharmacological Basis of Therapeutics*, Macmillan Publishing Co., New York, N.Y. (1975)].

Transmucosal, transdermal, intranasal, and rectal routes of administration of vasodilators according to the present invention avoids the first-pass effect allowing administration of the vasodilator a short time prior to the projected initiation of intercourse ("on demand") and eliminating the need for repeated administration of the drug. Methods of the present invention are thus more convenient and help minimize any side-effects that can arise as a result of continuous or daily administration of the drugs. In addition, methods of the present invention allow more spontaneity in sexual activity than allowed by other methods such as intracavernosal injection of vasodilators.

Formulations for effecting transmucosal delivery of vasodilators according to the present invention are well known in the art. For purposes of the present invention, "transmucosal delivery" generally refers to delivery of the drug to the oral or pharyngeal mucosa and includes buccal delivery, sublingual delivery, and delivery to the pharyngeal mucosa, but not to the stomach. Buccal delivery may be accomplished by preparing a tablet or lozenge comprising, for example, compressed lactose and an effective amount of one or more vasodilators. Other suitable tablet compositions include, but are not limited to, a combination of an effective dose of a vasodilator, and carrier substances, tablet-binding compounds and flavoring agents such as those described in U.S. Pat. No. 3,943,246 to Stürmer, which is incorporated herein by reference. Vasoactive agents may also be compounded with a variety of pharmaceutical excipients including binders such as gelatin and/or corn starch or pharmaceutically acceptable gums such as gum tragacanth. Vasoactive agents may also be combined in a hard candy (which may be dissolved in the mouth) or in a chewing gum, to provide buccal or sublingual delivery to the oral mucosa.

Vasodilators may also be administered transmucosally by impregnating a filter paper strip or a filter paper disc with an effective amount of a vasodilator. The filter paper strip or disc may then be placed between the cheek and gum (buccally) for delivery to the vasculature of the genitalia without encountering first-pass effects. Other transmucosal delivery systems such as lollipops (as described in U.S. Pat. No. 4,885,173 to Stanley) are well known in the art are expected to be useful in the practice of the present invention.

Transdermal administration of vasodilators according to the present invention also eliminates the "first-pass" effect occurring when drugs are administered orally or into circulatory flow leading to the liver.

Transdermal delivery systems are well known in the art and involve what are sometimes referred to as transdermal "patches". Exemplary transdermal patches typically comprise: (1) a impermeable backing layer which may be made up of any of a wide variety of plastics or resins, e.g. aluminized polyester or polyester alone or other impermeable films; and (2) a drug reservoir comprising, for example, a vasodilator in combination with mineral oil, polyisobutylene, and alcohols gelled with USP hydroxymethylcellulose. Other exemplary drug reservoir layers may comprise, for example, acrylic-based polymer adhesives with resinous crosslinking agents which provide for diffusion of the drug from the reservoir to the surface of the skin. The transdermal patch may also have a delivery rate-controlling membrane such as a microporous polypropylene disposed between the reservoir and the skin. Ethylene-vinyl acetate copolymers and other microporous membranes may also be used. Typically, an adhesive layer is provided which may comprise an adhesive formulation such as mineral oil and polyisobutylene combined with the vasoactive agent.

Other typical transdermal patches may comprise three layers: (1) an outer layer comprising a laminated polyester film; (2) a middle layer containing a rate-controlling adhesive, a structural non-woven material and the vasodilator; and (3) a disposable liner that must be removed prior to use. Transdermal delivery systems may also involve incorporation of highly lipid soluble carrier compounds such as dimethyl sulfoxide (DMSO), to facilitate penetration of the skin. Other exemplary carders include lanolin and glycerin.

Vasodilating drugs for use in transmucosal, transdermal, intranasal, or rectal delivery may be chemically modified by methods well known in the art to improve their lipid solubility and thus their ability to penetrate skin or mucosal surfaces.

Rectal suppositories are also useful in the practice of the present invention for administration by a route which bypasses the "first-pass" effect. Exemplary suppositories comprise a vasodilating drug combined with glycerin, glyceryl monopalmitate, glycerol, monostearate, hydrogenated palm kernel oil and fatty acids. Another exemplary suppository formulation includes ascorbyl palmitate, silicon dioxide, white wax, and cocoa butter in combination with an effective amount of a vasodilating drugs.

The present invention is also directed to the use of nasal sprays for the administration of the vasodilators. Exemplary nasal spray formulations comprise a solution of vasodilating drug in physiologic saline or other pharmaceutically suitable carder liquids. Nasal spray compression pumps are also well known in the art and can be calibrated to deliver a predetermined dose of the vasodilator solution.

The examples set forth below are intended to be illustrative of the present invention and are not intended to limit the scope of the invention as set out in the appended claims.

Example 1 describes the effect of transmucosally administered phentolamine mesylate on penile arterial velocity. Examples 2 and 3 describe the effect of buccally administered phentolamine mesylate on erectile ability in impotent men. Example 4 describes the use of a variety of vasodilators in the practice of the present invention. Example 5 addresses practice of the present invention in modulating erectile response in females.

EXAMPLE 1

Effect of Transmucosal Administration of Phentolamine Mesylate on Penile Arterial Velocity In order to assess whether or not buccally administered phentolamine mesylate could alter arterial blood flow in the penis, penile arterial velocity was measured close to the base of the right branch of the dorsal artery of the penis by doppler ultrasound velocimetry using a Diasonics 400 DRF (Diasonics, Milpitas, Calif.). Settings, incidence of doppler beam, and angle correction were maintained to achieved maximum velocity readings on each subject. The dorsal artery was selected for measurement because it was more accessible than the artery of the corpus cavernosum.

Figure 1:
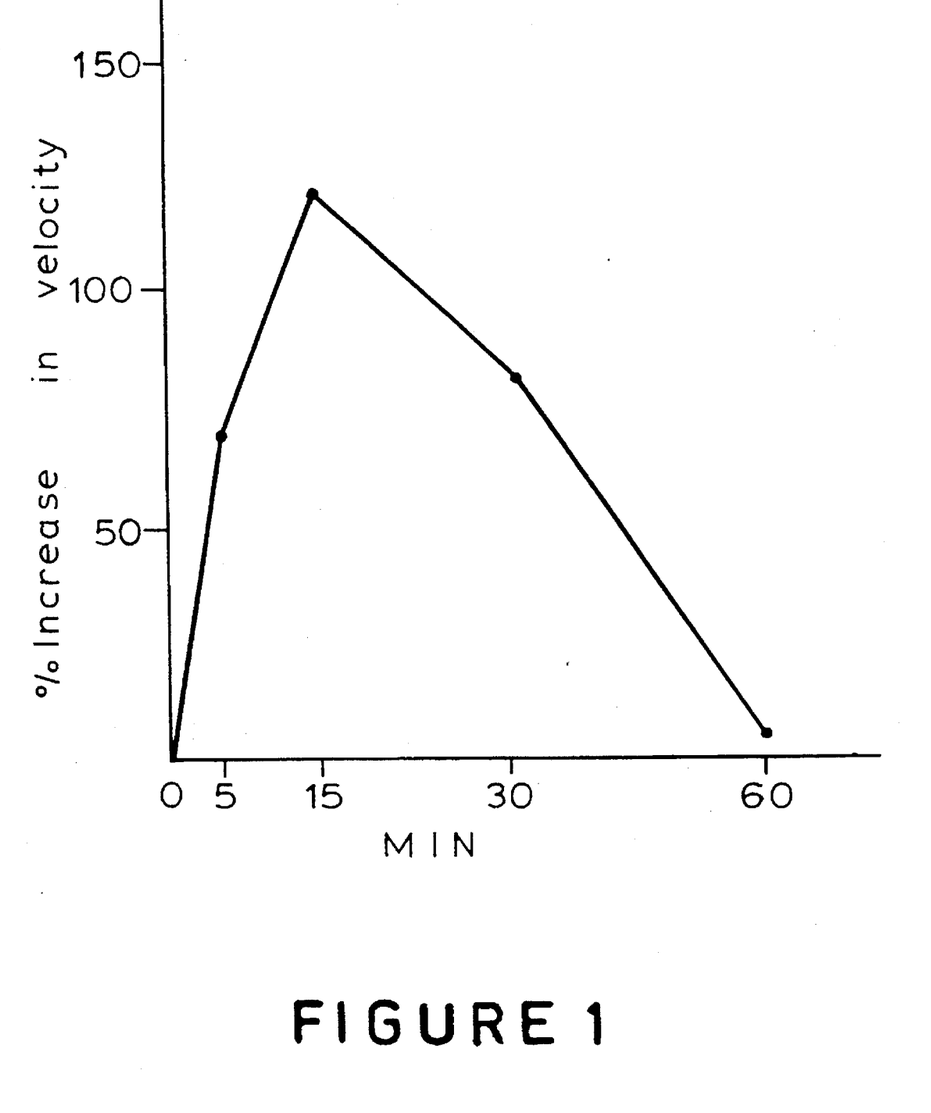
FIG. 1 is a graph depicting the percentage change in penile arterial blood velocity after buccal administration of a 20 mg dose of phentolamine mesylate.

Velocities were measured before the transmucosal (buccal) administration of phentolamine mesylate (20 mg) and at 5, 15, 45 and 60 minutes after administration of the drug. Mean initial velocity was 10.4 cm/sec. The data shown in FIG. 1 shows the percentage increase in penile artery velocity versus time after administration of phentolamine mesylate and represent the mean of triplicate readings in six impotent subjects.

The results show that, within five minutes of placing the tablet between the cheek and gum, arterial velocity rose by more than 50% above base line velocity. Within 25 minutes, arterial velocity peaked at more than 100% above base line velocity after which velocity began to fall, reaching pretreatment levels after 1 hour. Buccal administration of 20 mg of phentolamine mesylate is thus shown to provide a suitable means for rapidly altering penile arterial blood flow.

EXAMPLE 2

Effect of Transmucosal (Buccal) Administration of Phentolamine Mesylate on Male Erectile Ability The fact that buccal administration of 20 mg of phentolamine mesylate as in Example 1 resulted in a rapid increase in penile artery velocity supported utility of this route of administration of vasodilators in improving erectile ability in impotent men. Thus, studies were therefore conducted to determine the effect of transmucosal administration of phentolamine mesylate on erectile ability in impotent men.

All patients included in the study complained of an erectile dysfunction which either prevented vaginal penetration or was characterized by an inability to maintain an erection without ejaculation upon initiation of vaginal penetration. The duration of impotence was within a range of 0.5 years to 35 years in this patient population and the mean duration was 3.4 years.

Prior to administration of phentolamine mesylate or placebo, a medical history was taken, a genital examination was performed, and penile vascular status was determined. Vascular status was determined by measuring brachial and penile systolic closing pressures and calculating a penile brachial index (PBI). PBI was calculated by dividing the penile systolic pressure by the brachial systolic pressure. Plethysmographic crest times (CT) were measured with a Penilab IV plethysmograph (Parkes, Aloha Wash.). Crest time is the time in seconds from the trough of the penile blood pressure curve to the next peak. The normal range of crest times is from about 1 second to about 1.8 seconds. A PBI of >0.9 is considered normal while a PBI of <0.6 indicates vascular insufficiency.

For the purposes of this study, the patients were identified as having normal vascularity if both PBI and CT were in the normal range. Patients having both CT and PBI in the abnormal range were identified as having marked vascular insufficiency. Patients having one parameter in the abnormal range were identified as having moderate vascular insufficiency.

Age and diagnosis were generally not a factor in admission to the study, although patients with extreme age or severe penile vascular insufficiency were excluded. Patients having vascular or non-specific causes of impotence were admitted to the trial, as were patients having diabetes mellitus. Mean age of patients was 57.5 years (range: 25–74 years).

In order to test the effort of phentolamine mesylate on erectile ability, a single blind trial was conducted. Each patient was given two tablets; a placebo tablet comprising lactose alone, and a second lactose tablet containing 20 mg of phentolamine mesylate.

Patients were asked to place one tablet between the cheek and gum (buccal) 10–20 minutes before attempting coitus. Buccal administration was used as a paradigm of transmucosal delivery which, like all routes of delivery useful in the practice of the present invention, results in the drug reaching the vasculature of the target (genitalia) prior to passing through the liver. One or more days after using the first tablet, patients repeated the process with the second tablet. Patients were advised not to swallow the tablets or consume alcohol prior to using the tablets and were told not to expect erection without sexual stimulation.

Patients were told that either tablet might prove beneficial and were told to report results in terms of erection and vaginal penetration, partial erection, or failure to maintain an erection sufficient to permit vaginal penetration. Patients were also asked to report side effects. Results of this study are illustrated in Table 1 which shows the age, vascular status and effect of phentolamine mesylate on erectile ability in impotent men. In the righthand columns of Table 1, the number 1 indicates a report of erection and vaginal penetration, 2 indicates reported failure to achieve erection, and 3 indicates report of a partial erection.

TABLE 1

VASCULAR STATUS AND THE EFFECTS OF BUCCAL ADMINISTRATION OF PHENTOLAMINE ON PENILE ERECTILE ABILITY IN IMPOTENT MEN

| Patient Number | Age | Crest Time | Penile Brachial Indices Right | Penile Brachial Indices Left | Phentolamine (20 mg) | Placebo |
|---|---|---|---|---|---|---|
| 1 | 60 | 1.5 | 0.75 | 0.87 | 3 | 2 |
| 2 | 60 | 2.4 | 0.79 | 0.82 | 1 | 2 |
| 3 | 64 | 2.4 | 0.78 | 0.81 | 1 | 2 |
| 4 | 61 | 2.4 | 0.72 | 0.72 | 2 | 2 |
| 5 | 60 | 2.2 | 0.84 | 0.82 | 1 | 2 |
| 6 | 39 | 1.4 | 0.77 | 0.79 | 1 | 1 |
| 7 | 46 | 1.6 | 0.91 | 1.00 | 2 | 2 |
| 8 | 33 | 1.4 | 0.76 | 0.78 | 3 | 2 |
| 9 | 44 | 1.6 | 0.99 | 0.89 | 2 | 2 |
| 10 | 36 | 2.4 | 0.90 | 0.90 | 2 | 2 |
| 11 | 66 | 2.2 | 0.91 | 0.90 | 1 | 2 |
| 12 | 45 | 1.8 | 0.67 | 0.87 | 1 | 1 |
| 13 | 50 | 2.0 | 0.81 | 0.74 | 2 | 2 |
| 14 | 62 | 1.6 | 0.82 | 0.97 | 3 | 2 |
| 15 | 51 | 1.8 | 0.78 | 0.89 | 3 | 2 |
| 16 | 44 | 2.6 | 0.69 | 0.69 | 1 | 1 |
| 17 | 38 | 2.0 | 1.00 | 0.87 | 2 | 2 |
| 18 | 49 | 1.4 | 0.93 | 0.94 | 1 | 2 |
| 19 | 49 | 2.2 | 0.89 | 1.04 | 2 | 2 |
| 20 | 53 | 2.4 | 0.80 | 0.86 | 2 | 2 |
| 21 | 65 | 1.6 | 1.05 | 0.96 | 1 | 2 |
| 22 | 54 | 1.6 | 0.80 | 0.81 | 2 | 1 |
| 23 | 65 | 1.8 | 0.95 | 0.93 | 1 | 1 |
| 24 | 63 | 1.6 | 1.00 | 0.99 | 2 | 1 |
| 25 | 64 | 2.0 | 0.86 | 0.77 | 3 |  |
| 26 | 54 | 1.2 | 0.92 | 0.88 | 1 | 2 |
| 27 | 65 | 2.6 | 0.98 | 0.93 | 2 | 2 |
| 28 | 64 | 2.8 | 0.90 | 0.80 | 2 | 2 |
| 29 | 67 | 2.4 | 0.84 | 0.89 | 2 | 2 |
| 30 | 68 | 2.2 | 0.74 | 0.71 | 1 | 2 |
| 31 | 60 | 2.0 | 1.03 | 1.00 | 2 | 2 |
| 32 | 51 | 1.6 | 0.79 | 0.75 | 2 | 2 |
| 33 | 72 | 2.8 | 1.05 | 1.07 | 1 | 1 |
| 34 | 59 | 2.4 | 0.55 | 0.56 | 1 | 2 |
| 35 | 56 | 1.6 | 0.68 | 0.79 | 1 | 2 |
| 36 | 59 | 2.4 | 0.85 | 0.79 | 2 | 2 |

TABLE 1-continued

VASCULAR STATUS AND THE EFFECTS OF BUCCAL ADMINISTRATION OF PHENTOLAMINE ON PENILE ERECTILE ABILITY IN IMPOTENT MEN

| Patient Number | Age | Crest Time | Penile Brachial Indices Right | Left | Phentolamine (20 mg) | Placebo |
|---|---|---|---|---|---|---|
| 37 | 58 | 3.2 | 0.65 | 0.53 | 2 | 1 |
| 38 | 50 | 2.2 | 0.89 | 0.98 | 2 | 2 |
| 39 | 66 | 2.4 | 0.59 | 0.54 | 1 | 3 |
| 40 | 51 | 2.8 | 0.66 | 0.55 | 3 | 2 |
| 41 | 53 | 2.8 | 0.69 | 0.78 | 2 | 2 |
| 42 | 62 | 2.2 | 0.93 | 0.95 | 2 | 2 |
| 43 | 66 | 2.0 | 0.80 | 0.82 | 1 | 1 |
| 44 | 56 | 2.0 | 0.65 | 0.73 | 3 | 2 |
| 45 | 74 | 2.9 | 0.86 | 0.87 | 2 | 2 |
| 46 | 63 | 2.2 | 1.10 | 1.08 | 2 | 2 |
| 47 | 72 | 2.0 | 0.55 | 0.67 | 2 | 2 |
| 48 | 70 | 2.4 | 0.81 | 0.83 | 2 | 2 |
| 49 | 69 | 2.4 | 0.95 | 0.95 | 2 | 2 |
| 50 | 55 | 2.0 | 0.82 | 0.80 | 3 | 2 |
| 51 | 55 | 2.4 | 1.01 | 0.92 | 2 | 3 |
| 52 | 65 | 2.4 | 0.81 | 0.80 | 3 | 2 |
| 53 | 60 | 2.0 | 0.74 | 0.83 | 2 | 2 |
| 54 | 62 | 1.6 | 0.87 | 0.88 | 1 | 2 |
| 55 | 53 | 2.2 | 1.02 | 0.98 | 2 | 2 |
| 56 | 37 | 1.6 | 0.96 | 0.87 | 1 | 2 |
| 57 | 55 | 2.0 | 0.71 | 0.56 | 1 | 2 |
| 58 | 25 | 1.8 | 0.89 | 0.91 | 2 | 2 |
| 59 | 51 | 2.0 | 1.02 | 1.14 | 2 | 2 |
| 60 | 35 | 2.0 | 0.85 | 0.98 | 2 | 2 |
| 61 | 69 | 2.8 | 0.93 | 0.97 | 2 | 2 |
| 62 | 40 | 2.3 | 0.95 | 0.91 | 2 | 2 |
| 63 | 54 | 2.0 | 0.98 | 0.86 | 1 | 2 |
| 64 | 76 | 2.2 | 0.70 | 0.71 | 3 | 2 |
| 65 | 53 | 2.4 | 0.92 | 0.90 | 2 | 2 |
| 66 | 59 | 2.6 | 0.79 | 0.69 | 2 | 2 |
| 67 | 59 | 2.0 | 0.83 | 0.87 | 2 | 2 |
| 68 | 53 | 3.2 | 0.58 | 0.78 | 1 | 2 |
| 69 | 38 | 2.2 | 0.88 | 0.85 | 2 | 2 |

The data in Table 1 illustrates that buccal administration of 20 mg of phentolamine mesylate resulted in improved erectile ability within 10 minutes to 20 minutes after buccal administration of the drug. The response was characterized by improved erectile ability upon sexual stimulation and thus, the response closely mimicked the normal sexual response in men. The fact that the effect of the drug was seen within 10–20 minutes after a single administration can be characterized as a response occurring "on demand" in that multiple doses and/or a long waiting time before onset of improved erectile ability were not required. The rapid increase in penile artery velocity within five minutes of administration of phentolamine mesylate (as indicated in Example 1) suggests that improve erectile ability may actually occur sooner than 10 minutes after administration. The "on demand" aspect of the method of the present invention allows a more natural and more spontaneous approach to intercourse and eliminates the need for multiple doses, and thus, reduces the frequency of undesirable side effects. Although a 20 mg dose of phentolamine mesylate was used in the present study, doses from about 5 mg to about 80 mg of phentolamine mesylate are within the scope of the present invention as individual responsiveness to the drug may vary e.g., on the basis of total body weight and degree of vascular insufficiency.

The data set out in Table 1 was further analyzed to determine if the vascular status of the patients had any predictive value with respect to the efficacy of phentolamine mesylate in improving the erectile ability in impotent patients. The analysis showed that, of 16 total patients with normal vascular status, seven were successfully treated with phentolamine mesylate, six failed to respond, and three achieved partial erection. Of the 49 patients with vascular insufficiency, 15 were successful in achieving erection sufficient for vaginal penetration, while 29 failed. Five patients with vascular insufficiency achieved partial erection. The side effects seen in this study were infrequent and include, stuffy nose (6%), faintness or dizziness (2.3%) (relieved by lying down for 10–15 minutes) and vomiting 0.05%.

EXAMPLE 3

Effect of Buccal Phentolamine Mesylate and Impotence of Various Etiologies

Another single blind study was conducted in men having erectile dysfunction of various etiologies in order to further assess the efficacy of buccally administered phentolamine in ameliorating erectile dysfunction.

A mixed population of men having erectile dysfunction of various etiologies were given 3 filter paper strips impregnated with 20 mg of phentolamine mesylate and 3 placebo strips. The patients were not told which strips contained the drug and which strips were placebo. Patients were told to place one filter paper strip between the cheek and gum 10 minutes to 20 minutes prior to attempts to achieve erection. The treatment was deemed successful if an erection sufficient to affect vaginal penetration was achieved. The results are shown in Table 2.

TABLE 2

| Patient No. | Etiology | Result |
|---|---|---|
| 1 | Peyronie's Disease and associated erectile dysfunction | 2 |
| 2 | psychogenic | 1 |
| 3 | arteriogenic/psychogenic | 1 |
| 4 | neurogenic | 2 |
| 5 | arteriogenic | 1 |
| 6 | arteriogenic | 1 |
| 7 | * | 2 |
| 8 | * | 2 |
| 9 | * | 2 |
| 10 | * | 2 |
| 11 | * | 2 |
| 12 | psychogenic | No Report |
| 13 | arteriogenic | 1 |
| 14 | psychogenic | 1 |
| 15 | arteriogenic | 2 |
| 16 | psychogenic | 1 |
| 17 | psychogenic | 1 |
| 18 | arteriogenic/psychogenic | 1 |
| 19 | arteriogenic | 2 |
| 20 | psychogenic | 1 |
| 21 | arteriogenic | 2 |
| 22 | arteriogenic | 2 |
| 23 | arteriogenic/psychogenic | 2 |

* Prior to enrolling in this study, patients Nos. 7–11 were on a program of intracavernosal auto-injection using 20 μg of PGE-1 with perfect efficacy. These patients also suffered from severe cardiovascular disease.
1 = erection and vaginal penetration
2 = failure to achieve erection sufficient for vaginal penetration The results of this study establish that buccally administered phentolamine mesylate (20 mg) improved erectile ability in 36% of the patients reporting (excluding a total of two placebo responders). The results were most pronounced in patients with a diagnosis of psychogenic impotence wherein 5 of 5 patients reporting achieved an erection sufficient to vaginal penetration. Of those patients diagnosed as having arteriogenic impotence 3 of 7 patients showed improved erectile ability, with one of these patients also responding to placebo. Two of three patients diagnosed as having combined arteriogenic/psychogenic impotence showed improved erectile ability, with one of these patients also responding to placebo. Of the 5 patients in whom autoinjection of PGE-1 had shown perfect efficacy, none showed improvement in erectile ability with buccally administered phentolamine mesylate.

These results, when combined with those set out in Example 2, indicate that vasodilators such as phentolamine mesylate when administered via a route of administration which avoids the "first-pass" effect is effective in improving the onset of erectile ability in a significant percentage of impotent men and more particularly in men having psychogenic, arteriogenic, or combined psychogenic/arteriogenic impotence, the subpopulation of patients comprising the majority of cases of male impotence.

While useful in the treatment of impotence in males, the present invention is also useful in improving erectile ability in non-impotent men. It is well known that as men age, erectile ability may be altered. One manifestation of this decline in erectile ability is that the angle of erection subtended by the dorsal surface of the erect penis and the abdomen (erectile angles) increases with age. The method of the present invention, provides a means for improving erectile ability in non-impotent men by increasing blood flow to the penis, and thereby minimizing the erectile angle.

It should also be noted that filter strips impregnated with phentolamine mesylate lost their potency after several months of storage at room temperature in a paper bag.

EXAMPLE 4

Vasoactive Agents Useful in Modulating the Human Sexual Response

A number of other vasoactive agents may be used in the practice of the present invention based on their demonstrated efficacy as vasodilators. Useful vasodilating drugs include those generally classified as α-adrenergic antagonists, sympathomimetic amines and those agents which exhibit direct relaxation of vascular smooth muscle.

Exemplary α-adrenergic antagonists include phentolamine hydrochloride, phentolamine mesylate, phenoxybenzamine, tolazoline, dibenamine, yohimbine, and others. Phentolamine mesylate is preferred in the practice of the present invention. An exemplary sympathomimetic amine contemplated for use in the method of the present invention is nylidrin although other sympathomimetic amines having vasodilating activity are also comprehended by the invention.

Nicotinic acid (or nicotinyl alcohol) has a direct vasodilating activity which is useful in the practice of the present invention. Papaverine is also non-specific smooth muscle relaxant which has vasodilating activity and has been used to treat male impotence by direct injection into the corpus cavernosum either alone or in combination with other drugs such as phentolamine.

Organic nitrates such as nitroglycerine and amyl nitrate also have pronounced vasodilating activity by virtue of their ability to relax vascular smooth muscle. Other vasoactive drugs of use in the practice of the present invention include but are not limited to thymoxamine, imipramine, verapamil, naftidrofuryl, isoxsuprine, and others.

In the practice of the present invention, these vasoactive agents are administered by the transmucosal, intranasal, transdermal, or rectal routes of administration such that the agent reaches its site of action prior to entering the portal circulation, thereby avoiding the "first-pass" effect.

Appropriate doses of each vasoactive agents for each route of administration are readily determined by those of ordinary skill in the art. By way of illustration, in order to determine the appropriate dose of each of the vasodilating agents of the present invention, one of ordinary skill in the art may use as a starting point, the usual published dosage of the vasodilator. The usual oral doses for commercially available vasodilators can be found in the Physician's Desk Reference published annually by Medical Economic Data, Montvale N.J., and in the available medical literature.

By way of example, Pavabid® oral papaverine hydrochloride is available from Marion Merrell Dow and is normally administered at 150 mg every 12 hours to achieve its vasodilating effects.

The oral dose of Calon® (verapamil hydrochloride) available from Searle is determined by titrating the individual patient with from 120 mg to about 240 mg of drug every 12 hours, the specific dose depending on the individual patient's response to the drug.

Yohimbine hydrochloride available as Daytohimbin® (Dayton Pharmaceuticals), Yocon® (Palisades Pharmaceuticals), and Yohimex® (Kramer) are all administered orally as 5.4 mg three times a day.

Imipramine hydrochloride is available as Tofranil® from Geigy and is administered orally 4 times a day for a total dose ranging from 50 mg to about 150 mg per day.

Imipramine pamoate, also available from Geigy is administered in oral maintenance doses of 150 mg/day.

Using the established oral dosages as starting points, the optimal dosage for the specific route of administration can be determined by measuring baseline arterial blood flow in genital circulation of the patient prior to administration of the drug using a doppler ultrasound velocimeter as described in Example 1. Other methods such as thermography, plethysmography, radiometric or scintigraphic methods, and other methods well known in the art may also be utilized to assess blood flow in the genitalia. Having established base line blood flow, various dosages of the respective vasodilators may be administered by the routes of administration encompassed by the present invention and their effect on blood flow may be measured. The magnitude of the increase in blood flow necessary to modulate or enhance the sexual response in humans may vary from individual to individual, but is readily determined as described below. In addition, individual patients may be titrated with various dosages of the respective vasodilators until the optimum dosage is determined.

Vascular flow studies may also be coupled with assessments of sexual responsiveness as evidenced by the improvement of erectile ability in response to sexual stimulation.

EXAMPLE 5

Modulation of the Female Sexual Response

As discussed above, there are striking parallels between the vascular anatomy of male and female genitalia and in the erectile response facilitated by this vasculature. In both males and females, the erectile response takes place when under physical or psychological stimulation, blood flow to the genitalia increases by virtue of relaxation of smooth muscles in the arteries serving the genitalia.

The methods of the present invention may be used to improve or enhance the erectile response in women whose sexual response is impaired as evidenced by diminished capacity to produce sufficient vaginal lubrication to facilitate comfortable penile penetration and by other symptoms of impaired sexual responsiveness that may be correlated with the erectile response.

As in the case of male sexual response, in the absence of any clinically diagnosed dysfunction in the female erectile response, the methods of the present invention may be used to enhance the normal female sexual response. The "on demand" aspect of the present invention will allow a more rapid response to sexual stimulation along with heightened sensation associated with excitement and plateau stages of the female sexual response by virtue of the increased blood flow to the tissues.

In practice, enhancement of the female sexual response using the methods of the present invention are carded in much the same way as those described in Examples 2 and 3.

An effective vasodilating dose of a vasodilating agent is administered to a woman via the transmucosal, transdermal, intranasal, or rectal routes of administration. The appropriate doses of the particular vasodilating agent may be readily determined using methods described in Example 4. The female response may be measured using methods described in Masters, W. H. and Johnson, V. E., *Human Sexual Response*, Little, Brown, and Co., Boston (1966) which is incorporated herein by reference. Methods for measuring blood flow, including doppler ultrasonic velocimetry, thermography using for example an isothermal blood flow transducer, radioscintigraphic methods, photoplethysmography may be used as well as other methods well known in the art. In addition, measuring the contraction of the distal ⅓ as is characteristic of the plateau phase of female sexual response of the vagina may be measured using methods and equipment well known in the art including but not limited to strain gauges or other devices for measuring muscular contraction or muscle tension.

In addition, enhanced sexual response may be measured in a more subjective manner by simply asking the female subject to describe any change in sensation brought about by administration of the vasodilator by the methods of the present invention. Appropriate placebo controls should also be conducted to ascertain whether or not the effort is directly attributable to the administration of the vasodilator.

A preferred embodiment of the present invention involves the buccal administration of from about 5 mg to about 80 mg of phentolamine mesylate from about 1 minute to about 1 hour prior to, and in preparation for, intercourse. However any of the other routes of administration of any of the vasodilating agent included within the scope of the present invention may be used.

While this invention has been described by way of preferred embodiments, the examples set out herein are not intended to limit the scope of the invention which contemplates the use of any pharmacologic vasodilating drug capable of absorption into the systemic circulation upon administration of the drug via the transmucosal, transdermal, intranasal, or rectal routes of administration.

We claim:

1. In a method for improving sexual responsiveness in a human by administering a vasodilator agent to blood circulation in an amount effective to increase blood flow to the genitalia, the improvement comprising improving sexual responsiveness on demand by administering an effective amount of the agent by a route selected from the group consisting of oral mucosal, intranasal, and rectal.

2. The improvement of claim 1 wherein the vasodilating agent is selected from the group consisting of phentolamine mesylate, phentolamine hydrochloride, phenoxybenzamine, yohimbine, nitroglycerin, thymoxamine, nicotinyl alcohol, imipramine, verapamil, isoxsuprine, naftidrofuryl, tolazoline, and papaverine.

3. The improvement of claim 1 or 2 wherein the amount administered is effective for onset of increased blood flow to the genitalia within from about 1 minute to about 60 minutes following administration of the agent.

4. The improvement of claims 1, 2, or 3 wherein the human is a male.

5. The improvement of claims 1, 2, or 3 wherein the human is a female.

6. The improvement of claims 1, 2, or 3 wherein the vasodilator agent is phentolamine mesylate.

7. The improvement of claim 6 wherein the route of administration is oral mucosal.

8. The improvement of claim 7 wherein the effective amount is from about 5 mg to about 80 mg of phentolamine mesylate.

9. In a method for improving sexual responsiveness in an impotent male by administering a vasodilator agent to circulation in an amount effective to increase blood flow to the penis, the improvement comprising improving blood flow to the penis on demand by administering an effective amount of the agent by a route selected from the group consisting of oral mucosal, intranasal, and rectal.

10. The improvement of claim 9 wherein the vasodilating agent is selected from the group consisting of phentolamine mesylate, phentolamine hydrochloride, phenoxybenzamine, yohimbine, nitroglycerine, thymoxamine, nicotinyl alcohol, imipramine, verapamil, isoxsuprine, naftidrofuryl, tolazoline, and papaverine.

11. The improvement of claim 9 or 10 wherein the amount of vasodilating agent administered is effective to improve blood flow within from about 1 minute to about 60 minutes following administration of the agent.

12. In a method for improving sexual responsiveness in an impotent male by administering a vasodilator agent to blood circulation, the improvement comprising buccal administration of from about 5 mg to about 80 mg of phentolamine mesylate to the circulation whereby improvement of erectile ability in response to sexual stimulation is achieved within about 10 minutes to about 20 minutes after administration of phentolamine mesylate.

13. In a method for sexual responsiveness in an impotent male by administering a vasodilator agent to blood circulation, the improvement comprising buccal administration of 20 mg of phentolamine mesylate to the circulation whereby improvement of erectile ability is achieved in within about 10 minutes to about 20 minutes after administration of phentolamine mesylate.

14. A method for modulating the excitation and plateau phases of the female sexual response, the method comprising administering to blood circulation of a female a vasodilator agent in an amount effective to increase blood flow to the genitalia, the route of administration therefor being selected from the group consisting of transmucosal, transdermal, intranasal, and rectal.

15. The method of claim 14 wherein the vasodilating agent is selected from the group consisting of phentolamine mesylate, phentolamine hydrochloride, phenoxybenzamine, yohimbine, nitroglycerine, thymoxamine, nicotinyl alcohol, imipramine, verapamil, naftidrofuryl, isoxsuprine, tolazoline, and papaverine.

16. The method of claim 14 wherein the amount administered is effective for the onset of increased blood flow to the genitalia within from about 1 minute to about 60 minutes following administration of the agent.

17. The method of claim 15 wherein the vasodilating agent is phentolamine mesylate.

* * * * *

UNITED STATES PATENT AND TRADEMARK OFFICE
CERTIFICATE OF CORRECTION

PATENT NO.   :   5,565,466
DATED        :   October 15, 1996
INVENTOR(S)  :   Gioco et al.

It is certified that error appears in the above-identified patent and that said Letters Patent is hereby corrected as shown below:

Col. 1, line 44 "impotentia erectionis" should be --*impotentia erectionis*--.

Col. 2, line 30 "tolazoline o hydrochloride" should be --tolazoline hydrochloride--.

Col. 5, line 16 "serving the o" should be --serving the--.

Col. 6, line 55 "site of effect described below." should be --site of action prior to entering portal circulation, thereby avoiding the "first-pass" effect described below.--.

Col. 8, line 18 "carders" should be --carriers--.

Col. 8, line 37 "carder" should be --carrier--.

Col. 9, line 54 "vasculafity" should be --vascularity--.

Col. 10, in TABLE 1 insert --2-- in the twenty-fifth entry under the category Placebo.

Col. 15, line 20 "carded" should be --carried--.

UNITED STATES PATENT AND TRADEMARK OFFICE
CERTIFICATE OF CORRECTION

PATENT NO. : 5,565,466
DATED : October 15, 1996
INVENTOR(S) : Gioco et al.

It is certified that error appears in the above-indentified patent and that said Letters Patent is hereby corrected as shown below:

Col. 16, line 55 "method for sexual responsiveness" should be --method for improving sexual responsiveness--.

Signed and Sealed this

Twenty-ninth Day of July, 1997

Attest:

BRUCE LEHMAN

Attesting Officer      Commissioner of Patents and Trademarks